(12) United States Patent
Furrate et al.

(10) Patent No.: US 9,597,423 B2
(45) Date of Patent: Mar. 21, 2017

(54) ADAPTABLE DIFFUSER

(71) Applicant: Jayden, Inc., Dallas, TX (US)

(72) Inventors: Jamie Furrate, Dallas, TX (US);
Kristin Maples, Frisco, TX (US)

(*) Notice: Subject to any disclaimer, the term of this patent is extended or adjusted under 35 U.S.C. 154(b) by 158 days.

(21) Appl. No.: 14/316,761

(22) Filed: Jun. 26, 2014

(65) Prior Publication Data

US 2015/0374874 A1    Dec. 31, 2015

(51) Int. Cl.
*A61L 9/12* (2006.01)
*A61L 9/14* (2006.01)
*B65D 83/14* (2006.01)

(52) U.S. Cl.
CPC . *A61L 9/14* (2013.01); *A61L 9/12* (2013.01); *B65D 83/14* (2013.01)

(58) Field of Classification Search
CPC . A61L 9/14; A61L 9/12; B65D 83/14–83/267
USPC ......... 239/332, 340, 51.5; 222/626, 63, 649; 248/220.1
See application file for complete search history.

(56) References Cited

U.S. PATENT DOCUMENTS

| | | | | |
|---|---|---|---|---|
| 5,673,825 A * | 10/1997 | Chen | .......... | A61L 9/14 222/153.03 |
| 6,036,108 A * | 3/2000 | Chen | .......... | B65D 83/262 222/402.13 |
| 6,267,297 B1 * | 7/2001 | Contadini | .......... | A61L 9/12 222/646 |
| 6,785,911 B1 * | 9/2004 | Percher | .......... | A61L 9/14 222/180 |
| 7,798,424 B2 * | 9/2010 | Lin | .......... | A61L 9/14 222/129 |
| 2010/0226818 A1 * | 9/2010 | Miyagi | .......... | A61L 9/048 422/4 |
| 2012/0018530 A1 * | 1/2012 | Blaylock | .......... | A61L 9/122 239/7 |
| 2012/0168468 A1 * | 7/2012 | Wang | .......... | B60R 25/00 222/504 |

* cited by examiner

*Primary Examiner* — Steven J Ganey
*Assistant Examiner* — Juan C Barrera
(74) *Attorney, Agent, or Firm* — Braxton, Hilton, Perrone, PLLC

(57) ABSTRACT

A system and for diffusing. The system includes a diffuser body and two angled sides. The diffuser also includes a removable cover which is coupled to the diffuser body via a coupling device. Further, a shield is coupled to the diffuser body. The diffuser houses a container which is at least partially filled with a fragrance which is to be emitted by the diffuser. The removable cover hides the container from view. The diffuser is shaped to allow the diffuser to be placed in a corner. Further, because the cover can be removed, the cover can be customized and adjusted for a more aesthetically pleasing diffuser.

16 Claims, 4 Drawing Sheets

ADAPTABLE DIFFUSER

BACKGROUND OF THE INVENTION

Technical Field

The present invention relates to a system and method for a fragrance diffuser.

Description of Related Art

A fragrance diffuser sprays fragrance into a room. However, these diffusers are generally bulky, not aesthetically pleasing, and consequently, are generally only placed in laundry rooms, etc. Consequently, there is a need for an improved fragrance diffuser.

BRIEF DESCRIPTION OF THE DRAWINGS

The novel features believed characteristic of the invention are set forth in the appended claims. The invention itself, however, as well as a preferred mode of use, further objectives and advantages thereof, will be best understood by reference to the following detailed description of illustrative embodiments when read in conjunction with the accompanying drawings, wherein:

DETAILED DESCRIPTION

Several embodiments of Applicant's invention will now be described with reference to the drawings. Unless otherwise noted, like elements will be identified by identical numbers throughout all figures. The invention illustratively disclosed herein suitably may be practiced in the absence of any element which is not specifically disclosed herein.

Figure 1:
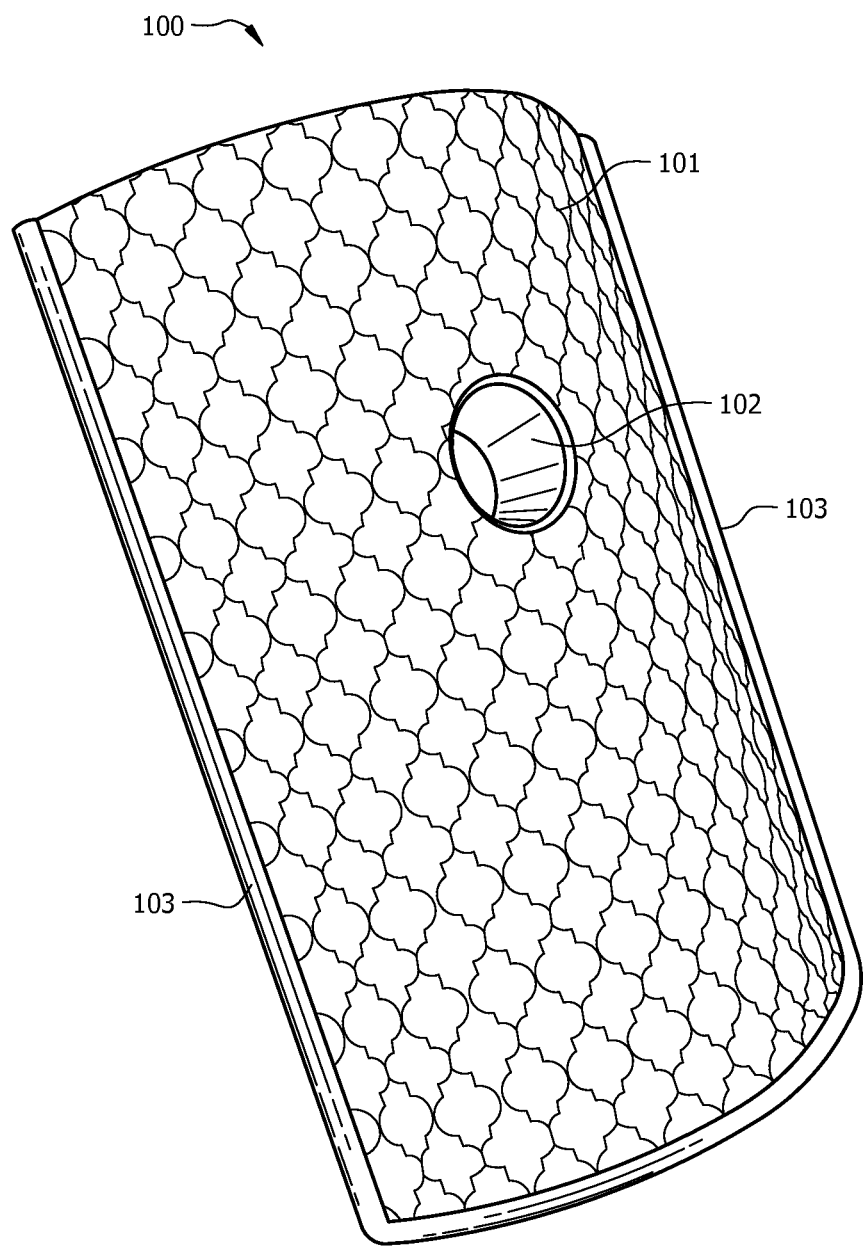
FIG. 1 is a front perspective view of a diffuser in one embodiment.

FIG. 1 is a front perspective view of a diffuser in one embodiment. A diffuser is a device which sprays a fragrance. The diffuser 100 can comprise any type of diffuser known in the art including automatic and manual diffusers. A fragrance, as used herein, refers to a fluid which is sprayed into an area for the purposes of enhancing or altering the areas smell. A fragrance includes perfumes, disinfectants, deodorizers, etc. A fragrance include fragrances with any medium, including oil based, water based, aerosol, etc.

As depicted the diffuser 100 comprises a cover 101. In one embodiment, the cover 101 comprises a removable cover. A removable cover is a cover which can be coupled and decoupled from the diffuser 100. A removable cover 101 has several advantages. First, because it is removable it can be replaced. As depicted, the cover 101 comprises a design. The cover 101 and its design and can be changed to match the color, design, or décor, of the room. For example, if the room in which the diffuser 100 is located is red, the user can select a red cover 101. The ability to change the cover 101 provides the diffuser 100 the ability to blend into the surroundings. Often, people do not want to draw attention to the diffusers. A bulky and plastic diffuser detracts from the elegance of a room. Consequently, many diffusers are limited to laundry rooms, restrooms, etc. However, the ability to camouflage, decorate, and customize the cover 101, allows the diffuser to be used in elegant rooms. An additional benefit of the cover is it provides an opportunity to advertise or display a brand, logo, or product. For example, if the diffuser is placed in a hotel, the name of the hotel can be located on the cover.

Virtually any design or color can be used on the cover 101. The cover 101 can comprise a smooth texture, a shiny gloss, a muted gloss, a textured surface, a painted surface, or a wooden surface. Any design, color, or texture used on a wall can be replicated with the cover 101. The cover 101 can comprise virtually any material including plastic, rubber, wood, pressed board, paper, paper with laminate, cardboard, etc. Virtually any material which can support a design can be utilized as a cover 101.

Second, because the cover 101 is removable it can be replaced if damaged. Thus, rather than discard the entire diffuser, the cover 101 can simply be replaced.

Third, as can be seen from FIG. 1, the cover 101 is the dominant viewable portion of the diffuser 100. The cover 101 hides the moving parts, containers, etc. of the diffuser 100. In one embodiment, when positioned in an upper corner of a room, the cover 101 and the bottom of the diffuser are visible. Accordingly, in one embodiment the bottom side of the diffuser 100 comprises a removable cover.

As depicted in FIG. 1, the cover 101 comprises a curved face. Because in one embodiment, and discussed in more detail below, the diffuser body comprises two angled sides, the curved face of the cover 101 offers a smooth transition from left to right. In some embodiments a curved face is aesthetically pleasing. Further, the curved face helps grip and secure the container in the desired location. In other embodiments the cover 101 comprises a straight face. The cover 101 can comprise virtually any desired shape.

As depicted in FIG. 1, the diffuser 100 comprises ridges 103 which couple the cover 101 to the diffuser body. As depicted, the ridges 103 comprise a thin gap through which the edges of the cover 101 can slide. The ridges 103 grip the edges of the cover 101 and secure the cover 101 in place. In one embodiment, and as depicted, the diffuser body comprises four sides: a top side, a bottom side, a left side, and a right side. As depicted, the ridges 103 cover two of the four sides of the diffuser 100. The top side of the diffuser 100 and the bottom side of the diffuser do not have ridges 103 so that the cover 101 can be positioned and removed from the top side or bottom side. When the cover 101 is lowered, the bottom edge of the cover 101 engages and couples with the bottom side of the diffuser 100. In some embodiments the bottom side of the diffuser 100 comprises a ridge which couples with the bottom edge of the cover 101. While a ridge 103 has been described, this is for illustrative purposes only and should not be limiting. Virtually any coupling device, which removeably couples the cover 101 to the diffuser 100 can be utilized. The coupling device includes, but is not limited to, ridges, screws, bolts, Velcro, adhesives, snap one, groves, hinges, etc.

As can be seen, the cover 101 comprises at least one hole. This hole aligns with a port 102. A port 102 is a device which guides the spray of the diffuser 100. Thus, when the diffuser 100 sprays a fragrance, the spray exits through the port 102 and through the aligned hole. The port 102 can comprise any shape. As depicted the port 102 comprises an oval shape, however, virtually any shape which allows the fragrance to flow can be utilized. The slope of the angled walls of the port 102 can be optimized such that the fragrance does not hit the sides of the walls of the port 102. Further, in one embodiment the nozzle is a pivoting nozzle to provide for increased spraying surface.

Figure 2:
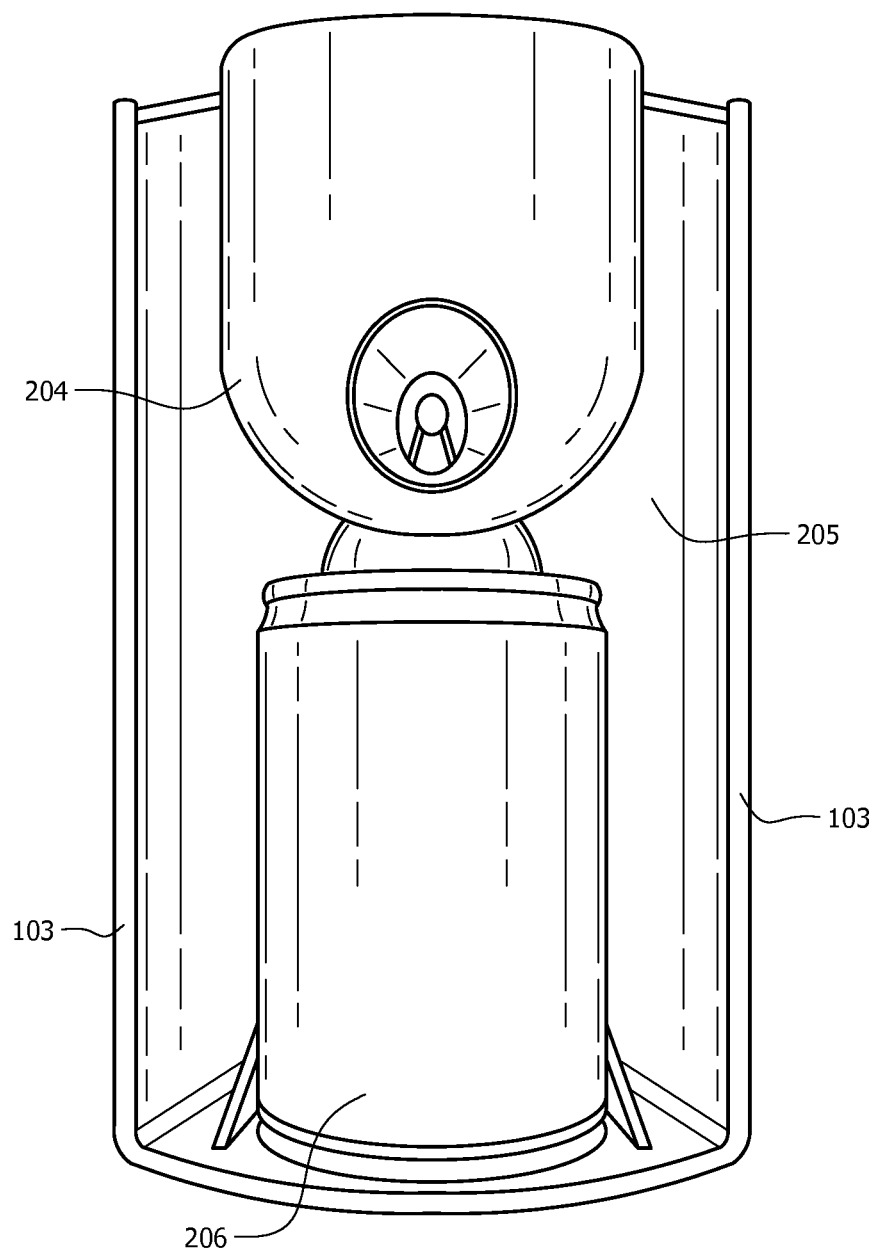
FIG. 2 is a front perspective view of a diffuser with the cover removed in one embodiment.

The port 102 can be better seen in FIG. 2. FIG. 2 is a front perspective view of a diffuser with the cover removed in one embodiment. As depicted, the port 102 is located on a shield 204. As depicted, the port 102 is integral with the shield 204. However, in other embodiments the port 102 is separate from the shield 204. In one embodiment, the port 102 is located on the cover 101.

The shield 204, as depicted, holds the port 102 and further helps secure the container 106. Further, as described below, in one embodiment the shield 204 conceals and covers the switch and controls of the diffuser 100.

The shield 204 can comprise virtually any material. It can comprise plastic, PVC plastic, rubber, metal, and other materials. The shield 204 can comprise the same material or a dissimilar material than the body 205 of the diffuser.

The shield 204 is coupled to the diffuser body 205 via any method or device known in the art. As depicted, the shield 204 is coupled via two hinges, but this is for illustrative purposes only and should not be deemed limiting. The hinges allow the shield 204 to be pivoted back to reveal the underneath container 206. In other embodiments the shield 204 is coupled with side hinges. In one embodiment the shield 204 comprises a bendable piece which can be bended or folded to the open position. In one embodiment, the shield 204 acts as a protective mechanism which protects the gears of other spraying mechanisms, protects the nozzle, and holds the container 206 in its desired location.

The diffuser body 205 houses the container 206 and couples the diffuser 100 to the support structure, such as a wall. The diffuser body 205 can comprise virtually any material, including but not limited to, plastic, rubber, metal, wood, pressed board, any material discussed previously, etc.

In one embodiment, and as depicted, the ridges 103 are integrally made with the diffuser body 205. Such an embodiment decreases on the number of manufacturing parts, which reduces manufacturing complexity and cost.

Coupled to the diffuser body 205 is the container 206. The container 206 is any container which holds the fragrance to be sprayed. In some embodiments the container 206 is under pressure such as that when the nozzle is depressed, the fragrance is sprayed. The height of the container 206 can vary. In one embodiment the container 206 is about an inch in height to about 7 inches in height, depending on the desired volume. The pressure within the container 206 can comprise any acceptable pressure for typical fragrance containers. The pressure can range from about atmospheric pressure to several atmospheres. As depicted, the diffuser body 205 has rails at the bottom to help couple and secure the container 206. The container is further secured by the cover 204. In some embodiments the diffuser body 205 has straps, bands, inserts, or other objects which further grab and secure the container 206 within the diffuser body 205. In one embodiment, the container comprises grips 412 (depicted in FIG. 4) which grip the container 206 and hold it in place. As depicted, the grips 412 secure the nozzle of the container 206 under tension to secure the container 206.

Figure 3:
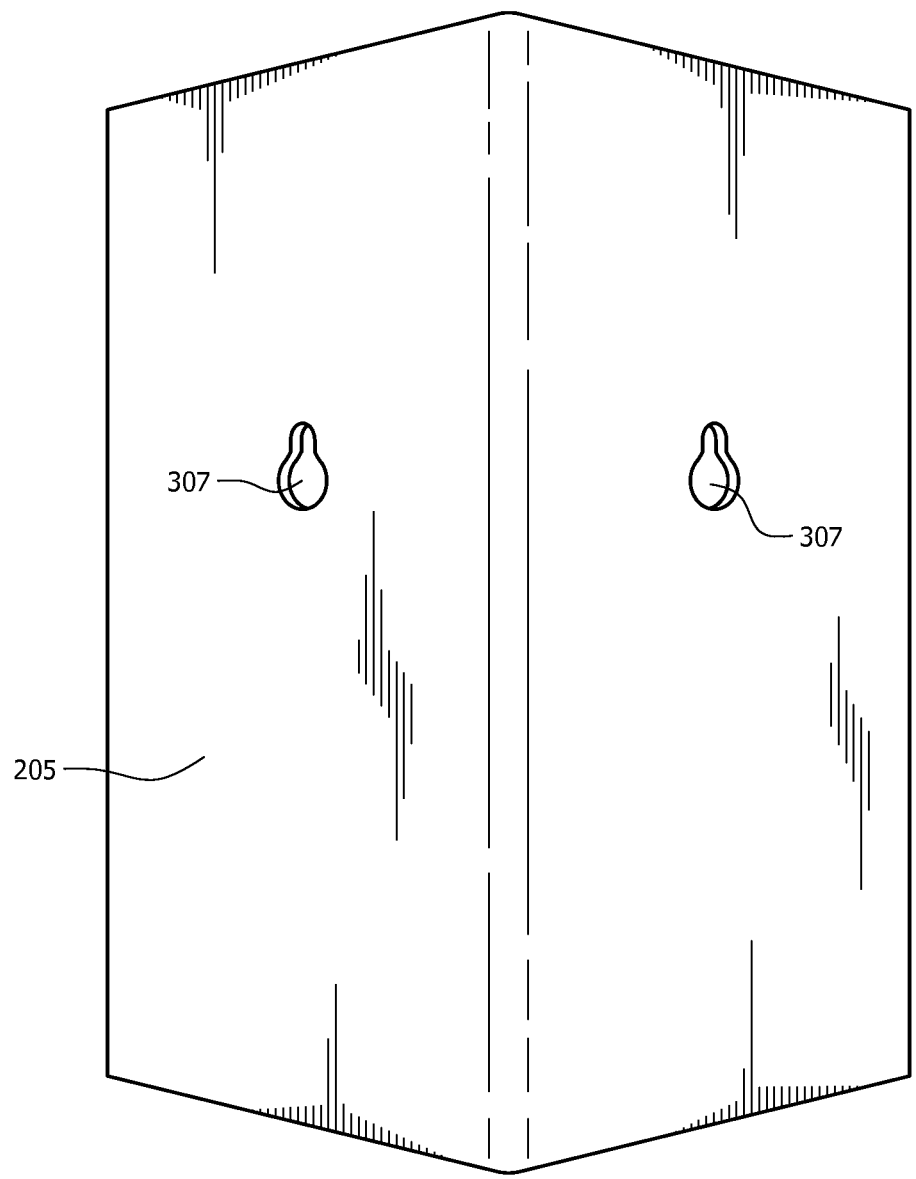
FIG. 3 is a back perspective view of a diffuser in one embodiment.

FIG. 3 is a back perspective view of an embodiment of a diffuser. As seen in this embodiment, the rearward facing sides of diffuser body 205 are constructed to conform to a corner configuration of walls in a room or closet or perpendicular sides of a cabinet or shelving. As depicted, two substantially perpendicular sides of diffuser body 205 include slots 307. Diffuser 100 may be hung with the rearward facing side of diffuser body 205 flush against the wall by inserting screws, nails, bolts, etc. into a wall or other mounting surface. Alignment of screws with slots 307 is necessary to facilitate insertion of screws into slots 307 and achieving an effective securing of diffuser 100 at the point of interest. Slots 307 are constructed to allow a screw head, as one example, to pass inside of diffuser body 205 and the slide upwardly to effectively lock the screw head in place by virtue of the weight of diffuser 100. This description of the manner and structure related to mounting diffuser 100 is not intended to be limiting. There are numerous alternative mechanisms for mounting diffuser 100, such as use of a bracket sized to receive all or part of diffuser body 205. For example, in one embodiment a bracket is first attached to a wall. The bracket comprises hooks or other attaching devices which couple with the diffuser body 205 to secure the diffuser 100 to the wall. Alternatively, a variety of other fasteners or adhesive materials or glues may be used to secure diffuser body 205 to an area of interest, such as straps, hook and loop material such as Velcro, or other suitable items or material. Further, diffuser body 205 may be mounted to pre-existing items that are mounted at or near the area of interest, such as a motion detector or other similar device. Still, in other embodiments, the diffuser 205 can be rest upon a pre-existing object such as a dresser, table, shelf, etc.

The ability to position the diffuser 100 in a corner is a significant advantage. As noted, previous diffusers were unseemly, and accordingly, relegated to bathrooms, laundry rooms, etc., where décor was not a concern. However, by being able to be placed in a corner, the diffuser appears less bulky, more aesthetically pleasing, and in some embodiments, less noticeable. In some embodiments, the diffuser 100 can be placed in the upper corner of a room, for example, which may not be noticed by house guests. This advantage allows a diffuser 100 to be placed in more formal rooms, such as living rooms, dens, etc., without detracting from the décor of the room.

While one embodiment has been discussed wherein the rearward facing sides of the diffuser body 205 are substantially perpendicular, this is for illustrative purposes only. If two walls intersect at a 60° angle, or at a 120° angle, the diffuser body 205 can be angled to accommodate the angled intersection. Accordingly, in one embodiment the diffuser body 205 comprises at least two sides which intersect at an angle. The angle can vary from about 30° to about 140°. In one embodiment the angle ranges from about 60° to about 120°. In one embodiment the angle is about 90°.

As depicted in FIG. 3, each side of the diffuser body 205 comprises at least one slot 307. As noted, this is for illustrative purposes only and should not be deemed limiting. In some embodiments only a single side will comprise the slot 307. In still other embodiments, the slot 307, or other attaching devices, are located above or below the diffuser body 205. For example, in one embodiment the slot 307 is located on the top side of the diffuser body 205. In such embodiments a screw, as an example, is secured into the ceiling, and the diffuser body 205 is then coupled to the ceiling via at least one slot 307 located on the top side of the diffuser body 205. Thus, in some embodiments rather than being secured from the rearward facing side, as illustrated in FIG. 3, the diffuser 100 is secured from a top side or bottom side. In one embodiment a bracket is secured to a ceiling, and the bracket comprises hooks or other attaching devices which couple with the top side of the diffuser body.

The size of the diffuser can vary depending upon the desired application. In one embodiment the diffuser has a height as measured from the bottom of the diffuser body 205 to the top of the diffuser body 205 of between about 3 inches to about 14 inches. In one embodiment the diffuser has a width as measured from the left side of the diffuser 100 to the right side of the diffuser 100, as depicted in FIG. 1, of between about 3 inches to about 14 inches. In one embodiment the diffuser has a maximum depth, measured as the largest distance between the cover 100 and the diffuser body 205 of between about 2 inches to about 8 inches. These dimensions are for illustrative purposes only and should not be deemed limiting. The size of the diffuser can be adjusted depending on the desired application.

Figure 4:
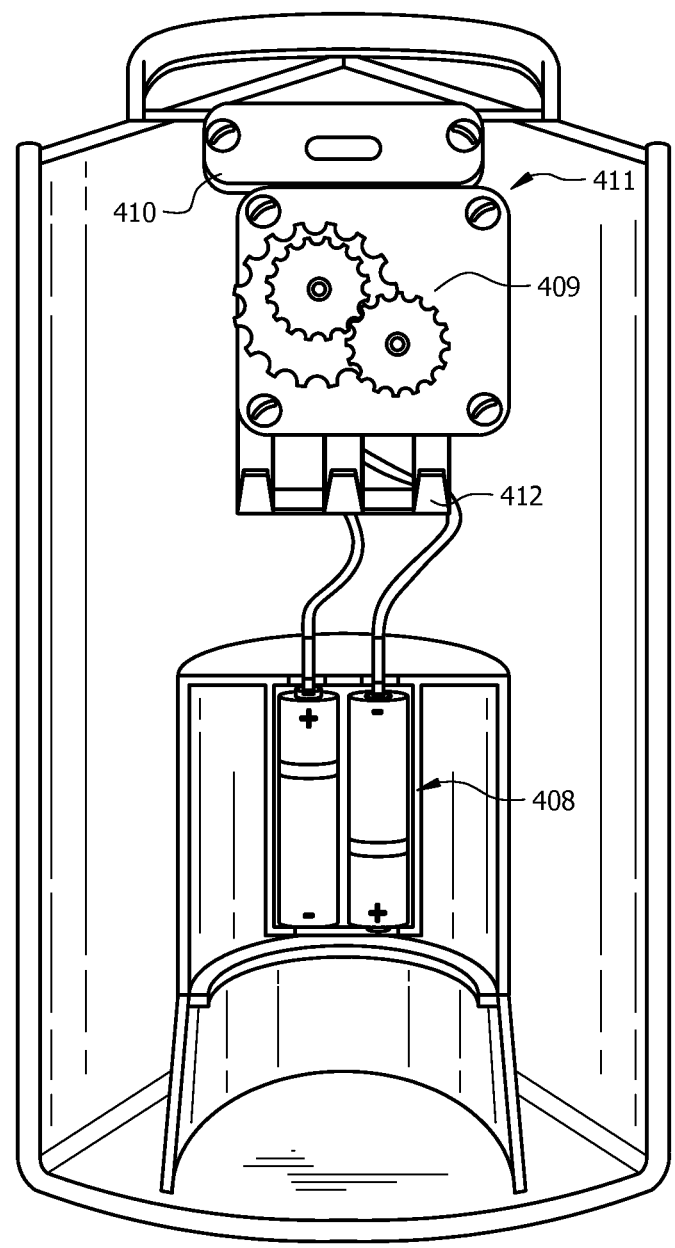
FIG. 4 is a front perspective view of a diffuser with the container removed in one embodiment.

FIG. 4 is a front perspective view of a diffuser with the container removed in one embodiment. As seen in FIG. 4, the diffuser 100 contains several internal components that enable effective operation. The diffuser 100 includes a power supply 408 disposed within the diffuser body 205. In one embodiment, the power supply 408 comprises one or more common household batteries. In other embodiments, power may be supplied to a diffuser 100 though small solar panels suitable for small commercial items or the diffuser 100 may be hardwired to a residential or commercial electrical system.

Continuing with FIG. 4, the diffuser 100 includes a spraying mechanism 409 to cause a spray of fragrance at various intervals. In one embodiment, spraying mechanism 409 is an electro-mechanical timer including a gear assembly that causes regular emission of fragrance. The gears can comprise any suitable material including plastic, injectable mold plastic, polyoxymethylene and other such plastics, rubber, etc. In one embodiment, rotation of the gears causes a mechanical arm to depress the container nozzle, allowing fragrance to be emitted. The spraying mechanism 409 can comprise any device which controls and allows fragrance to be emitted from the container 206. The spraying mechanism 409 includes mechanical, electrical, or chemical devices which depress the valve of the container 206. In other embodiments the spraying mechanism 409 comprises a valve. In other embodiments, diffuser 100 may be equipped with a motion detector that in conjunction with small electronic components cause activation of port 102 to emit a fragrance when motion by the spraying mechanism 409 is detected. The diffuser 100 may be equipped with other small electro-mechanical devices, such as a sound activated spray assembly powered by the power supply 408 that cause spraying of fragrance upon a desired passage of time or the occurrence of a certain event. FIG. 4 also depicts a switch 410 that controls the mode of operation of diffuser 100. In one embodiment the switch 410 is a two way switch comprising an off and an on position. In other embodiments the switch 410 comprises at least a three-way switch, such as a four-way switch. In such switches, the switch comprises an off position and two or more "on" positions. In one embodiment, the two or more on positions comprise a first automatic spray position, and a second automatic spray position, wherein the frequency of spraying is different in the first and second automatic spray positions.

The on positions, in one embodiment, differ by the frequency of the spray which is emitted. For example, in one embodiment the four way switch comprises a high, medium, and low frequency rate. The low frequency causes fragrance to be emitted every 32 minutes. The medium frequency, in one embodiment, cause the fragrance to be emitted every 16 minutes. The high frequency, in one embodiment, causes fragrance to be emitted every 8 minutes. In one embodiment, depending upon the size of the container, the high frequency needs the container replaced every week, the medium frequency needs replacement every 2 weeks, and the low frequency needs replacement every 4 weeks. Those skilled in the art will understand that volume and rate of emission can be adjusted.

In one embodiment, the diffuser 100 will not spray when the switch 410 is placed in the off position. When the switch 410 is placed in one of the "on" positions, spraying will occur in accordance with the parameters controlled by the spraying mechanism 409. As discussed above, depending on the spraying mechanism 409 selected, spraying will occur automatically based on the frequency specified. The spraying can occur automatically according to passage of time, detection or motion, sound, light or other event.

In one embodiment, the diffuser 100 includes a plunger (not depicted) or manual activator to cause spraying of the contents of container 206 as desired without reliance on spraying mechanism 409. In one embodiment, manual activation of the plunger to emit fragrance may be desirable in the event of battery failure or emission of larger volumes of fragrance. In one embodiment the plunger sticks out from the diffuser such that it is accessible without removing the shield. In one embodiment, the plunger sticks out from the top of the diffuser.

While the invention has been particularly shown and described with reference to a preferred embodiment, it will be understood by those skilled in the art that various changes in form and detail may be made therein without departing from the spirit and scope of the invention.

ADDITIONAL DESCRIPTION

The following clauses are offered as further description of the disclosed invention.

Clause 1. A system for diffusing, said system comprising:
a diffuser body comprising two angled sides;
a removable cover coupled to the diffuser body with a coupling device;
a shield coupled to the diffuser body.

Clause 2. The system of any proceeding or preceding clause wherein said removable cover comprises a hole.

Clause 3. The system of any proceeding or preceding clause wherein said shield comprises a port.

Clause 4. The system of any proceeding or preceding clause wherein said coupling device comprises ridges located on said diffuser body.

Clause 5. The system of any proceeding or preceding clause wherein said diffuser body comprises four sides along its perimeter, a top side, a bottom side, a left side, and a right side.

Clause 6. The system of any proceeding or preceding clause wherein said ridges are located on said left side, said right side, but are not located on said top side of said diffuser body.

Clause 7. The system of any proceeding or preceding clause wherein said cover comprises a curved face.

Clause 8. The system of any proceeding or preceding clause wherein said two angled sides comprise an angle between about 30° and about 120°.

Clause 9. The system of any proceeding or preceding clause wherein said two angled sides comprise an angle of about 90°.

Clause 10. The system of any proceeding or preceding clause wherein said two angled sides comprises at least one slot.

Clause 11. The system of any proceeding or preceding clause wherein said shield is coupled to said diffuser body via hinges.

Clause 12. The system of any proceeding or preceding clause further comprising a power source.

Clause 13. The system of any proceeding or preceding clause further comprising a removable container.

Clause 14. The system of any proceeding or preceding clause wherein said removable container comprises a fragrance.

Clause 15. The system of any proceeding or preceding clause further comprising a switch.

Clause 16. The system of any proceeding or preceding clause further comprising a spraying mechanism.

Clause 17. The system of any proceeding or preceding clause wherein said spraying mechanism allows for automatic spraying.

Clause 18. The system of any proceeding or preceding clause further comprising at least a three-way switch.

Clause 19. The system of any proceeding or preceding clause wherein said at least three-way switch comprises an off position, a first automatic spray position, and a second automatic spray position, wherein the frequency of spraying is different in the first and second automatic spray positions.

Clause 20. The system of claim 1 further comprising a plunger for manual activation.

We claim:

1. A system for diffusing, said system comprising:
   a diffuser body comprising two rearward facing angled sides;
   a removable cover coupled to the diffuser body with a coupling device;
   a shield coupled to the diffuser body; wherein said angled sides are constructed to conform to a corner configuration;
   and wherein said two angled sides comprise an angle between about 30° and about 120°;
   wherein said diffuser body is shaped to be placed in a corner, wherein one end of said angled sides intersect at said angle, and wherein a second end of each of angled sides is coupled to said removable cover.

2. The system of claim 1 wherein said removable cover comprises a hole.

3. The system of claim 1 wherein said shield comprises a port.

4. The system of claim 1 wherein said cover comprises a curved face.

5. The system of claim 1 wherein said two angled sides comprise an angle of about 90°.

6. The system of claim 1 wherein said two angled sides comprises at least one slot.

7. The system of claim 1 further comprising a power source.

8. The system of claim 1 further comprising a removable container.

9. The system of claim 8 wherein said removable container comprises a fragrance.

10. The system of claim 1 wherein said body comprises a V-shaped cross-section.

11. The system of claim 1 further comprising a spraying mechanism.

12. The system of claim 11 wherein said spraying mechanism allows for automatic spraying.

13. The system of claim 11 further comprising at least a three-way switch.

14. The system of claim 13 wherein said at least three-way switch comprises an off position, a first automatic spray position, and a second automatic spray position, wherein the frequency of spraying is different in the first and second automatic spray positions.

15. A system for diffusing, said system comprising:
    a diffuser body comprising two rearward facing angled sides;
    a removable cover coupled to the diffuser body with a coupling device;
    a shield coupled to the diffuser body; wherein said angled sides are constructed to conform to a corner configuration;
    and wherein said two angled sides comprise an angle between about 30° and about 120°; wherein said coupling device comprises ridges located on said diffuser body, and wherein said removable cover comprises side edges, and wherein said ridges comprise a thin gap through which the edges of the cover can slide and wherein said diffuser body comprises four sides, a top side, a bottom side, a left side, and a right side, and wherein said two rearward facing angled sides comprise the left side and the right side, wherein said left side and said right side intersect at said angle, and wherein said intersection is conformed to a corner configuration, and wherein removable cover couples to said left and right sides.

16. The system of claim 15 wherein said ridges are located on said left side, said right side, but are not located on said top side of said diffuser body.

* * * * *